United States Patent [19]

Wicheta et al.

[11] 4,428,929

[45] Jan. 31, 1984

[54] NEW ORAL CLEANSING MEDIUM FOR WEARERS OF PARTIAL AND FULL DENTURES

[76] Inventors: William E. Wicheta, P.O. Box 5280, Austin, Tex. 78763; Alvin L. Boyd, P.O. Box 5280, Austin, Tex. 78749

[21] Appl. No.: 457,066

[22] Filed: Mar. 4, 1983

[51] Int. Cl.$^3$ ............................ A61K 7/16; A61K 7/22
[52] U.S. Cl. ........................................ 424/49; 424/54; 424/56
[58] Field of Search ...................................... 424/49–58

[56] References Cited

U.S. PATENT DOCUMENTS

| 4,187,287 | 2/1980 | Schreiber et al. | 424/49 |
| 4,275,059 | 6/1981 | Flora et al. | 424/204 |
| 4,289,640 | 9/1981 | Falivene | 252/95 |
| 4,387,107 | 6/1983 | Klein et al. | 424/338 |
| 4,391,798 | 7/1983 | Tauss et al. | 424/54 |

OTHER PUBLICATIONS

A.D.A. Accepted Dental Therapeutics (38th Ed.) Sep. 1979, Chicago, Ill., pp. 264–265 Sweetening Agents, Saccharin, pp. 270–271 Detergents–Sodium lauryl Sulfate, pp. 272–273 Mucilaginous Substances–Methylcellulose, pp. 276–278 Essential Oils–Methyl Salicylate, p. 279 Preservatives–Methylparaben, pp. 339–341 Dentifrices.

*Primary Examiner*—Shep K. Rose

[57] ABSTRACT

This invention is a cleansing agent specifically for wearers of partial and complete dentures, whose gums, hard and soft palates, tongue and all inner mouth surfaces require thorough cleaning when the partial or full dental appliances are removed from the mouth.

1 Claim, No Drawings

NEW ORAL CLEANSING MEDIUM FOR WEARERS OF PARTIAL AND FULL DENTURES

DESCRIPTION OF THE INVENTION

There are specific powders, pastes, gels and liquids manufactured to clean natural teeth, artificial dentures and dental appliances. All have some active ingredient or abrasive to remove tartar, stains, and undesirable elements from dental surfaces, be they artificial appliances or real, natural teeth. Many of these ingredients, among them diatomaceous earth, fluoride compounds, chalk, formaldehyde, and even abrasives of aluminum compounds, are deliberately harsh and strong to perform a specific function in removal of stains, plaque, tartar, etc., from hard dental/denture surfaces.

This invention is a formula designed specifically to be a gentle cleanser of sensitive, tender living tissue in the mouth cavity, where harsh chemicals and abrasives are not necessary.

This invention is a formula which can be prepared either in the form of a clear gel, a colored gel, a white translucent paste, or a colored paste. The formula can be packaged in a jar or, more preferably, in a tube, as are most regular tooth pastes.

The gel or paste, containing no controlled substances, would be available to the consumer through normal retail sources wherever dental items are sold, and available without prescription.

This invention would make available to partial and full denture wearers a pleasant, tasteful and effective oral cleanser. Surveys indicate that denture wearers must now resort to harsh pastes (made for cleaning teeth and dentures) to cleanse their mouths, and especially, the oral mucosa. This invention is a formula prepared for no other purpose than to cleance the oral cavity. It is not formulated to clean teeth and dentures, and has no harsh chemicals or abrasives in its formula.

The formula is similar in appearance and consistency to most gels when prepared as a gel, and similar to most toothpastes when prepared as a paste. Mixing procedures determine visual appearance and consistency and whether or not a gel or a paste is the final result.

Taste of the formula is determined by flavoring added.

Color of the formula is determined by the omission of (clear or translucent) or addition of color to the basic formula.

All ingredients in the formula are comparatively inexpensive, abundant and easily obtainable. No special equipment is required to manufacture or package the medium other than normal equipment and machinery maintained and used by manufacturers of regular tooth and denture cleansing pastes.

Specific formulation prepared for testing actual denture wearing patients was a green, wintergreen-flavored gel. Patients used and tested the green gel on moist, soft toothbrushes (just as they would have used any toothpaste) applying the foaming gel to inner mouth tissues.

Objects of the Invention

An object of the invention is to provide a gentle cleansing medium for denture wearers, when dentures are removed from the mouth, to remove all undesirable elements from sensitive mouth tissues: food particles, denture adhesive residue and particles, sloughed-off dead cells and bacteria. Inner mouth tissues that must be thoroughly cleansed for maximum daily oral hygiene are gums, upper palate and mucosa covering the mandible, tongue and particularly those sensitive surfaces where dentures bear directly on soft tissue and tissue over bone surfaces.

Another object of the invention is to cleanse the senitive oral tissues, often irritated by ill-fitting dentures, or mouth areas suffering from poor oral hygiene of the patient in need of oral hygiene instruction, without further irritating those areas, but rather to provide a sense of healing to the areas.

A further object of the invention is to provide a medium that, through its foaming action, helps to float out and remove food particles, denture adhesive residue and particles and dead tissue cells, and thereby remove most elements in the mouth that tend to cause or are the source of bad breath.

Another object of the invention is to provide in the formula a breath freshner that will give the user a pleasant breath and to help establish a feeling of social well-being and acceptance.

Still another object of the invention is to give the user a pleasant tingling taste in the mouth during the application of the medium, as well as to provide a lingering, tangy aftertaste, heightening the positive psychological advantages of having a pleasant breath. The aftertaste is diminishing, of course, as are all dental cleansing media and oral mouth washers, and cannot be formulated to provide permanently fresh taste in the oral cavity.

Since smell (olfactory sense) is critical to taste, a further object of the invention is to smell acceptable and inviting to most personal sensitivities and preferences. Formula ingredients provide the taste and smell requirements.

Description of Formula Development and Testing

Over a 4-year period, early 1979 through late 1982, eleven formulas were prepared, tested and discarded as unacceptable. Formula No. 12 was acceptable in all aspects, and was found to meet all standards and goals originally set by the joint inventors, which were:

Formula had to:
1. Be easily obtainable to consumers.
2. Be inexpensive to elderly on limited income.
3. Cleanse sensitive living oral tissues thoroughly, gently.
4. Be free of harsh chemicals.
5. Taste good, with a tingling, fresh characteristic.
6. Look good, with acceptable color and texture, with strong foaming action.
7. Provide a pleasant, lingering aftertaste.
8. Provide a pleasant breath.
9. Consist of inexpensive, easily obtainable ingredients for inexpensive manufacture.
10. Be formulated of non-carcinogenic or suspect chemicals.
11. Be of standard, already accepted consistency, flavor and color.
12. Be manufactured and packaged by current machinery owned by existing companies.
13. Be eligible for immediate acceptance and endorsement by American Dental Association.
14. Be a good product, particularly beneficial for the elderly who are the largest age group with dentures and who have the greatest need for this new cleanser.

Formula No. 12 was tested by 30 patients of Dr. William E. Wicheta, D.D.S., joint inventor. Each patient, a partial or full denture wearer, was given a small tube of the formula and a test report form to complete after about 2 weeks of using the formula.

The testing formula was prepared in the following measures:
Methyl cellulose—1.5 g.
Water—35.0 mls.
Saccharin—80.0 mgs
Methyl salicylate—35.0 drops
Methyl parabens—0.02 g.
Sodium lauryl sulfate—1.0 g.
Triethanolamine—1.0 ml.
Food color, green—1.0 drop Sufficient formula was prepared for testing by all patients for the 2-week testing period. Order of mixing and procedure followed was:
1. Add saccharin to water. Heat until disolved.
2. Add methyl cellulose to warm solution (#1).
3. Add methyl parabens and sodium lauryl sulfate to #2. Allow 2–5 minutes for complete dissolution. Solution appears cloudy.
4. Allow to cool and for mixture to gel.
5. Add triethanolamine and methyl salicylate. Gel turns white.
6. Add green food color.

In preparing the base solution above, the following details should be observed:
1. Weigh saccharin and measure water. Add saccharin to water and heat slightly until completely dissolved. Do not overheat as overheating will break down saccharin.
2. After saccharin is dissolved in water, add methyl cellulose and continue low heat until methyl cellulose is also in solution.
3. Weigh methyl parabens and sodium lauryl sulfate. Add to warm solution, above. Solution will turn cloudy, requiring 2 to 5 minutes for total dissolution.

Using base solution, above, a cloudy (translucent) gel or a clear gel can be obtained by following these steps:

For Cloudy Gel:
1. Remove contents of base (step No. 3, above) and allow to cool. Refrigeration will cool and set a gel in about 15 minutes or less.
2. Add methyl salicylate to gel. Mix well. Gel becomes cloudy.
3. Add triethanolamine to above mixture. Mix well.
4. Add food color. Mix well. A cloudy (translucent) gel, similar to a paste, results.

For Clear Gel:
1. Add methyl salicylate to warm base solution.
2. Stir slightly. (Note: methyl salicylate is insoluble.)
3. After gel forms, add triethanolamine. Mix well.
4. Add food color. Mix well. A clear gel results.

Quantitative analysis of the formula, by weight, is:

| Ingredient | Percent by Weight |
|---|---|
| Water | 84.152% |
| Methyl salicylate | 6.27% |
| Methyl cellulose | 3.6% |
| Triethanolamine | 2.89% |
| Sodium lauryl sulfate | 2.4% |
| Food color (green) | .45% |
| Saccharin | .19% |

| Ingredient | Percent by Weight |
|---|---|
| Methyl Parabens | .048% |

Purpose and role of each ingredient in formula:
1. Methyl parabens. Colorless. A bacteriostatic agent, to prevent bacteria growth in formula. A preservative.
2. Saccharin. Colorless in solution. A sweetener. To add taste, flavor to gel.
3. Food Color. A combination of FD&C Yellow #5 and FD&C Blue #1. To add green color to be compatible with wintergreen flavor of methyl salicylate.
4. Sodium lauryl sulfate. Colorless. A soap. A surfactant to cleanse by foaming and lifting. A cleansing agent.
5. Triethanolamine. Colorless oil. A foam booster to enhence foaming action of sodium lauryl sulfate.
6. Methyl Cellulose. Colorless. A filler to add bulk to formula.
7. Methyl Salicylate. Colorless. Oil of wintergreen. A flavoring agent to add tingle and zesty taste. (This is the only ingredient in formula that is not water soluble. It is an emulsion in the formula.)
8. Water. Colorless. A thinner to bring gel to proper consistency and to put chemicals into solution.

Results of testing were measured by prepared report filled out by each of the 30 patients. Direct physical examination of oral tissues was performed by Dr. Wicheta, joint inventor, before and after test-use of formula number 12.

General results were positive. No negative effects on mouth tissues were observed by Dr. Wicheta, and although no curative powers are claimed for nor expected of the formula, in some instances oral tissues had actually shown an improvement, due mostly to regular cleansing and toothbrush massage received during continual testing program. Those patients showing tissue rejuvenation most probably had practiced poor or lax dental hygiene habits before the test. One female patient had never removed her partial denture since original application, so tissue degeneration had occurred due to total lack of cleansing procedures! Patients indicated a wide home-use variety of denture and tooth cleaners, from strong stain-removers and regular paste and powder preparations, to salt-and-soda.

Of the 30 patients testing the formula, 14 were men. 16 were women. The age ranges were:

|  | Under 30 | 31–40 | 41–50 | 51–60 | over 60 | Total |
|---|---|---|---|---|---|---|
| Males | 3 | 2 | 3 | 5 | 1 | 14 |
| Females | 1 | 2 | 5 | 4 | 4 | 16 |
| Total | 4 | 4 | 8 | 9 | 5 | 30 |

They were asked to evaluate the formula on 8 characteristics, assigning a value of Good (G), Acceptable (A), Poor (P).

Males tended toward higher evaluation in all categories than the female patients. This could probably be explained by the fact that women's senses tend to be more sensitive and their opinions more critical (from their roles as food preparers and their daily associations with cosmetics and fragranges?).

Specific evaluations rendered by both groups were:

| | MALES (14) | | | | | | | | | | | | | | | | | |
|---|---|---|---|---|---|---|---|---|---|---|---|---|---|---|---|---|---|---|
| | Under 30 | | | 31-40 | | | 41-50 | | | 51-60 | | | Over 60 | | | Totals | | |
| | G | A | P | G | A | P | G | A | P | G | A | P | G | A | P | G | A | P |
| Color | 3 | | | 2 | | | 2 | 1 | | 5 | | | 1 | | | 13 | 1 | |
| Smell | 2 | 1 | | 2 | | | 3 | | | 4 | 1 | | 1 | | | 12 | 2 | |
| Taste | 3 | | | 2 | | | 2 | 1 | | 5 | | | 1 | | | 13 | 1 | |
| Foaming | 3 | | | 2 | | | 3 | | | 5 | | | 1 | | | 14 | | |
| Cleansing | 3 | | | 1 | 1 | | 3 | | | 4 | 1 | | 1 | | | 12 | 2 | |
| Breath Freshener | 2 | 1 | | 2 | | | 3 | | | 4 | 1 | | 1 | | | 12 | 2 | |
| After Taste | 3 | | | 2 | | | 2 | 1 | | 5 | | | 1 | | | 13 | 1 | |
| Overall Strength | 3 | | | 2 | | | 3 | | | 5 | | | 1 | | | 14 | | |

| | FEMALES (16) | | | | | | | | | | | | | | | | | |
|---|---|---|---|---|---|---|---|---|---|---|---|---|---|---|---|---|---|---|
| | Under 30 | | | 31-40 | | | 41-50 | | | 51-60 | | | Over 60 | | | Totals | | |
| | G | A | P | G | A | P | G | A | P | G | A | P | G | A | P | G | A | P |
| Color | | 1 | | 1 | 1 | | 4 | 1 | | 2 | 2 | | 3 | 1 | | 10 | 6 | |
| Smell | | 1 | | 1 | 1 | | 5 | | | 4 | | | 4 | | | 14 | 2 | |
| Taste | 1 | | | 2 | | | 2 | 3 | | 3 | 1 | | 4 | | | 12 | 4 | |
| Foaming | | 1 | | 2 | | | 5 | | | 2 | 2 | | 4 | | | 11 | 5 | |
| Cleansing | 1 | | | 1 | 1 | | 5 | | | 4 | | | 4 | | | 15 | 1 | |
| Breath Freshener | 1 | | | 2 | | | 3 | 1 | 1 | 3 | 1 | | 3 | 1 | | 12 | 3 | 1 |
| After Taste | | 1 | | 2 | | | 3 | 2 | | 2 | 2 | | 4 | | | 11 | 5 | |
| Overall Strength | 1 | | | 1 | 1 | | 5 | | | 3 | 1 | | 4 | | | 14 | 2 | |

A strong rating of Good predominated all characteristics. Out of the 30 reports only one Poor was given: to Breath Freshening by a woman in the 41-50 group.

While a few preferences for other colors were expressed, (blue, pink) the pateints gave a strong acceptance of the green color used in the test formula. A unanimous score of Good was given to Overall Quality, with many patients verbally expressing complete satisfaction with the formula in follow-up office calls with Dr. Wicheta.

One interesting, but expected, result was that the older group (51-60, over 60) of both sexes had a higher preference for a stronger taste, due, more than likely, to diminishing sensitivity of aging taste buds.

Having described our invention, and what we desire to secure by Letters Patent, we claim:

1. A new and improved chemical formula prepared from and of the following ingredients, listed in descending quantitative analytical order of

| | |
|---|---|
| Water | 84.152% |
| Methyl salicylate | 6.27% |
| Methyl cellulose | 3.6% |
| Triethanolamine | 2.89% |
| Sodium lauryl Sulfate | 2.4% |
| Food Color (Green - a combination of FD&C Yellow #5 and FD&C Blue #1 | .45% |
| Saccharin | .19% |
| Methyl parabens | .048% |
| | 100.000% | that can be produced as a transparent gel, or as a translucent gel, and that is intended to be used primarily as a cleansing preparation in paste form of a gel consistency for application to all inner oral cavity surfaces and tissues of the hard and soft palates, the gums and the tongue of persons who wear partial or full dentures and dental prostheses, said formula is to be used when the dentures have been removed from the mouth, for maximum application and benefits directly to mouth tissues, particularly those areas covered or obscured by the dentures, the said formula, having no harsh chemicals or abrasives in its component parts which are intended to remove dental plaque, tartar and stains, and is instead a gentle, stimulating formula prepared especially to benefit sensitive mouth tissues by thorough foaming and cleansing and removal of irritating food particles, denture adhesive residue, sloughed-off dead cells and tissues and most halitosis-causing bacteria, and thereby helping to elimate the so-called "denture breath," and the said formula has the further benefits of providing a breath-freshener, and of introducing an immediate feeling of freshness and a pleasant, tingling, zesty taste in the mouth, that will linger after mouth tissues are cleansed, and is designed and formulated to be a complete oral cavity cleanser, especially of the soft tissue, to be used instead of commercial denture and dental cleansers for improved oral hygiene practices by denture and dental appliance wearers, and its gentle formulation, even if applied directly to healthy natural teeth and all oral tissue surfaces, will do no harm, but will cleanse and freshen the mouth parts, and formula is designed for mass market availability and sale directly to public without special prescription.

* * * * *